United States Patent
Dakka et al.

(10) Patent No.: US 7,276,638 B2
(45) Date of Patent: Oct. 2, 2007

(54) MULTI-COMPONENT MOLECULAR SIEVE CATALYST COMPOSITIONS AND THEIR USE IN AROMATICS REACTIONS

(75) Inventors: Jihad M. Dakka, Whitehouse Station, NJ (US); James C. Vartuli, Schwenksville, PA (US); John S. Buchanan, Lambertville, NJ (US); Jose G. Santiesteban, Baton Rouge, LA (US); Doron Levin, Annandale, NJ (US); Lorenzo C. DeCaul, Langhorne, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 6 days.

(21) Appl. No.: 11/392,804

(22) Filed: Mar. 29, 2006

(65) Prior Publication Data

US 2006/0270881 A1    Nov. 30, 2006

Related U.S. Application Data

(62) Division of application No. 10/299,170, filed on Nov. 19, 2002, now Pat. No. 7,074,739.

(51) Int. Cl.
*C07C 2/66* (2006.01)
(52) U.S. Cl. .................... 585/467; 585/469
(58) Field of Classification Search ........... 585/467, 585/469
See application file for complete search history.

(56) References Cited

U.S. PATENT DOCUMENTS

| | | | |
|---|---|---|---|
| 3,702,886 A | 11/1972 | Arguaer et al. |
| 3,930,987 A | 1/1976 | Grand |
| 4,076,842 A | 2/1978 | Plank et al. |
| 4,358,397 A | 11/1982 | Chu |
| 4,397,827 A | 8/1983 | Chu |
| 4,399,059 A | 8/1983 | Chu |
| 4,440,871 A | 4/1984 | Lok et al. |
| 4,954,325 A | 9/1990 | Rubin et al. |
| 5,993,642 A | 11/1999 | Mohr et al. |
| 6,180,828 B1 | 1/2001 | Hidaka et al. |
| 6,388,156 B1 | 5/2002 | Ou et al. |
| 6,423,879 B1 | 7/2002 | Brown et al. |
| 6,459,006 B1 | 10/2002 | Ou et al. |
| 6,471,941 B1 | 10/2002 | Boix et al. |
| 6,844,291 B2 | 1/2005 | Levin et al. |
| 6,906,232 B2 | 6/2005 | Levin et al. |
| 2003/0171633 A1 | 9/2003 | Xu et al. |
| 2004/0097769 A1* | 5/2004 | Ou et al. ............... 585/454 |
| 2004/0097770 A1 | 5/2004 | Dakka et al. |
| 2005/0101818 A1 | 5/2005 | Levin et al. |
| 2005/0255991 A1 | 11/2005 | Levin et al. |

FOREIGN PATENT DOCUMENTS

| | | |
|---|---|---|
| EP | 0 671 208 | 9/1995 |
| WO | WO 98/29370 | 7/1998 |
| WO | WO 01/64340 | 9/2001 |
| WO | WO 03/074176 | 9/2003 |

* cited by examiner

*Primary Examiner*—Elizabeth D. Wood
(74) *Attorney, Agent, or Firm*—Michael Kerns

(57) ABSTRACT

The invention relates to a process for producing alkylated aromatic hydrocarbons, preferably with an oxygen or sulfur containing alkylating agent, in the presence of a multi-component molecular sieve catalyst composition that includes a molecular sieve and an active metal oxide. The invention is also directed to methods of making and formulating the multi-component molecular sieve catalyst composition useful in producing alkylated aromatics.

70 Claims, No Drawings

US 7,276,638 B2

MULTI-COMPONENT MOLECULAR SIEVE CATALYST COMPOSITIONS AND THEIR USE IN AROMATICS REACTIONS

This application is a divisional of U.S. application Ser. No. 10/299,170, filed Nov. 19, 2002, now U.S. Pat. No. 7,074,739, which is hereby incorporated by reference.

FIELD OF THE INVENTION

The present invention relates to a conversion process utilizing a multi-component molecular sieve catalyst composition to alkylate aromatics. The invention is also directed to a method of making the molecular sieve catalyst composition by physically mixing solids or particulates comprising at least one active metal oxide with one or more molecular sieve materials.

BACKGROUND OF THE INVENTION

A variety of processes for alkylating aromatics using conventional aluminosilicate molecular sieve catalysts are commercially available. Various aromatic compounds are either naturally present in or are traditionally produced from petroleum feedstock by catalytic reforming processes.

Aromatics alkylation is an important procedure for producing many useful chemical products. For example, para-xylene, which can be produced by alkylating toluene with methanol, constitutes an important starting material for manufacturing synthetic polyester fibers, films; and resins. These polyester materials have many practical, well known uses, such as in fabrics, carpets, and apparel. Other alkylated aromatics have similar roles.

Methanol, the preferred alcohol for para-xylene production from a toluene feedstock, is typically synthesized from the catalytic reaction of hydrogen, carbon monoxide and/or carbon dioxide in a methanol reactor in the presence of a heterogeneous catalyst. For example, in one synthesis process methanol is produced using a copper/zinc oxide catalyst in a water-cooled tubular methanol reactor.

Molecular sieves are porous solids having pores of different sizes including crystalline molecular sieves such as zeolites, as well as carbons and oxides. The most commercially useful molecular sieves for the petroleum and petrochemical industries are crystalline molecular sieves. Crystalline molecular sieves in general have a one-, two-, or three-dimensional crystalline pore structure having uniformly sized pores of molecular scale within each dimension. These pores selectively adsorb molecules that can enter the pores and exclude those molecules that are too large.

Examples of some potentially useful molecular sieves for aromatics alkylation include aluminosilicate molecular sieves as described in co-pending U.S. patent application Ser. No. 09/866,907 (ITQ-13) and in U.S. Pat. No. 3,702,886 (ZSM-5), U.S. Pat. No. 4,076,842 (ZSM-23), U.S. Pat. No. 4,397,827 (ZSM-48), and U.S. Pat. No. 4,954,325 (MCM-22), all of which are herein fully incorporated by reference. Aluminosilicate molecular sieves, also known as zeolites, contain a three-dimensional microporous crystalline framework structure of $[SiO_4]$ and $[AlO_4]$ corner sharing tetrahedral units. Zeolites are generally synthesized by the hydrothermal crystallization of a reaction mixture of silicon and aluminum sources. Other metallosilicate molecular sieves with various metals (such as, for example, gallium, iron, and/or boron) substituted for aluminum in some portion of the crystalline framework are also known in the art.

Aluminum and phosphorus containing molecular sieve crystals (for example, ALPO and SAPO) can be produced by the hydrothermal crystallization of a reaction mixture of silicon, aluminum, and phosphorus sources along with at least one templating agent as described, for example, in U.S. Pat. No. 4,440,871, which is herein fully incorporated by reference.

Molecular sieves are often formed into molecular sieve catalyst compositions to improve their durability and to facilitate handling in commercial conversion processes. These molecular sieve catalyst compositions are formed by combining a molecular sieve with a matrix material and/or a binder. Although the use of binders and matrix materials are known for use with molecular sieves to form molecular sieve catalyst compositions useful in alkylating aromatics, these binders and matrix materials typically only serve to provide desired physical characteristics to the catalyst composition and have little to no effect on conversion and selectivity of the molecular sieve.

Many of the toluene alkylation processes use catalytic materials which are prone to rapid catalyst deactivation, usually due to coke formation, under typical reaction conditions and, therefore, require constant regeneration. This regeneration requirement usually necessitates the use of higher cost technology such as fluid bed reactors wherein the catalyst is continuously regenerated.

Although a variety of treatments have been disclosed for improving conversion, improving product selectivity, and/or reducing coke formation, there is still a significant problem with rapid catalyst de-activation due to coke formation at the reaction conditions required for alkylation of aromatics. It would therefore be desirable to have an improved molecular sieve catalyst composition having longer lifetimes and, preferably, also having better conversion rates, product selectivity, and commercially desirable operability and cost advantages.

SUMMARY OF THE INVENTION

This invention provides for a multi-component molecular sieve catalyst composition, a method for making or formulating the multi-component molecular sieve catalyst composition, and a process for using the multi-component molecular sieve catalyst composition to produce one or more alkylated aromatics.

In one embodiment the invention is directed to a method for making the multi-component molecular sieve composition of the invention by combining, contacting, mixing, or the like, a molecular sieve and at least one active metal oxide, preferably a non-acidic metal oxide. Preferably the molecular sieve is synthesized from the combination of two or more of a silicon source, an aluminum source, and a phosphorous source, optionally in the presence of a templating agent, and the active metal oxide is an oxide of a Group 2, Group 3, Group 4, Lanthanide Series, or Actinide Series metal. More preferred active metal oxides are combinations of a Group 4 metal oxide with one or more selected from Group 2, Group 3, Lanthanide Series, or Actinide Series metal oxides. Even more preferred are i) zirconium and/or hafnium oxides combined with a Group 3 metal oxide such as scandium, lanthanum, or yttrium metal oxide or ii) yttrium oxide. More preferably, the molecular sieve is an intermediate pore size aluminosilicate molecular sieve and the metal oxide is a zirconium and/or hafnium metal oxide co-precipitated with lanthanum oxide. Even more preferably, the active metal oxide is a co-precipitated combination of zirconium and lanthanum oxides, and the molecular sieve composition is a ZSM-5 catalyst modified as described U.S. Pat. No. 6,423,879, which is herein fully incorporated by reference.

In another embodiment the invention relates to a method for making a multi-component molecular sieve catalyst composition by combining, contacting, mixing, or the like, a molecular sieve, a matrix material, a binder, and at least one active metal oxide, wherein the active metal oxide is different from both the binder and the matrix material. Preferably, the active metal oxide is a non-acidic oxide of a Group 2, Group 3, Group 4, Lanthanide Series, or Actinide Series metal, and the molecular sieve is synthesized from the combination of two or more of a silicon source, an aluminum source, and a phosphorous source, optionally in the presence of a templating agent. In a more preferred embodiment, the molecular sieve and the binder and/or matrix material are made into a formulated molecular sieve catalyst composition that is then contacted, mixed, combined, spray dried, or the like, with at least one active metal oxide, preferably an active non-acidic Group 2, Group 3, Group 4, Lanthanide Series, and/or Actinide Series metal oxide, and more preferably a Group 4 metal oxide such as hafnium or zirconium metal oxide combined with a Group 2, Group 3, Lanthanide Series, or Actinide Series metal oxide.

In one more embodiment, the multi-component molecular sieve catalyst composition, formulated with a binder and/or matrix or otherwise, of the invention, discussed above, has a Half-life Enhancement Index (HLEI) significantly greater than catalyst compositions without an active metal oxide, that have, by definition, a HLEI of 1. HLEI is the ratio of the half-life of the multi-component molecular sieve catalyst composition described herein to that of the molecular sieve or molecular sieve catalyst composition in the absence of an active metal oxide. Determination of HLEI is discussed later in this patent specification.

In still another embodiment of the invention, a multi-component molecular sieve catalyst composition is made by a method comprising the steps of: (i) synthesizing a molecular sieve by the method comprising the steps of: (a) forming a first reaction mixture of at least two of the group consisting of a silicon source, a phosphorous source, and an aluminum source, optionally containing one or more templating agents, and (b) removing the molecular sieve from the first reaction mixture; (ii) producing an active metal oxide by the method comprising the steps of: (a) forming a second reaction mixture of at least one active metal oxide precursor, (b) removing an active metal oxide from the second reaction mixture, and (iii) combining the molecular sieve and the active metal oxide. Preferably the active metal oxide is calcined prior to combining the molecular sieve and the active metal oxide.

In yet another embodiment, the invention is directed to a process for alkylating aromatics in the presence of any of the above multi-component molecular sieve catalyst compositions described above. In particular, the process involves alkylating aromatics, preferably toluene, with an alkylating agent, preferably an oxygen- or a sulfur containing alkylating agent, more preferably an alkylating agent comprising an alcohol, and most preferably an alkylating agent comprising methanol, in the presence of one or more of the multi-component molecular sieve catalyst compositions discussed above.

The invention is also directed to a composition of matter of any one of the multi-component molecular sieve catalyst compositions described above. The invention is further directed to a multi-component molecular sieve catalyst composition comprising the use of at least one active metal oxide in combination with a molecular sieve, optionally including a matrix material and/or a binder, in which the active metal oxides are different from the matrix material and/or the binder, for use in alkylating aromatics using an oxygen- or sulfur-containing alkylating agent.

DETAILED DESCRIPTION OF THE INVENTION

Introduction

This invention is directed toward a multi-component molecular sieve catalyst composition, a method for making or formulating the multi-component molecular sieve catalyst composition, and a process for alkylating aromatics using the multi-component molecular sieve catalyst composition. It has been found that combining a molecular sieve with an active metal oxide results in a multi-component molecular sieve catalyst composition capable of alkylating one or more aromatics preferably in the presence of oxygenates, more particularly methanol, with a longer half-life than the molecular sieve alone. The preferred active metal oxides are those having a Group 2 (for example calcium and magnesium), Group 3 (for example scandium, yttrium, and lanthanum), Group 4 (for example zirconium and hafnium), Lanthanide Series (for example cerium, praseodymium, and neodymium), and/or Actinide Series (for example thorium and protactinium) metal from the Periodic Table of Elements using the IUPAC format described in the *CRC Handbook of Chemistry and Physics,* 79th Edition, CRC Press, Boca Raton, Fla. (1998). Also, surprisingly, the multi-component molecular sieve catalyst compositions have longer lifetimes, at least in part because they are less susceptible to coke formation which is well known to reduce catalyst activity. It has also been discovered that the multi-component molecular sieve catalyst compositions are often more selective to para-xylene when toluene is used as the feedstock. In this regard, in particular in the conversion of toluene to at least para-xylene, the production of less desirable ortho- and meta-xylene is reduced.

Molecular Sieves

Molecular sieves have various chemical, physical, and framework characteristics. Molecular sieves have been classified by the Structure Commission of the International Zeolite Association according to the rules of the IUPAC Commission on Zeolite Nomenclature. A framework-type describes the topology and connectivity of the tetrahedrally coordinated atoms constituting the framework and makes an abstraction of the specific properties for those materials. Molecular sieves for which a structure has been established are assigned a three letter code and are described in the *Atlas of Zeolite Framework Types,* 5th edition, Elsevier, London, England (2001), which is herein fully incorporated by reference.

Non-limiting examples of these molecular sieves include intermediate pore size molecular sieves having a pore size in at least one dimension from about 5 Å to about 7 Å, including, for example, AEL, EUO, FER, HEU, MEI, MEL, MFI, MFS, MTT, MTW, MWW, and TON structure type molecular sieves. Non-limiting examples of specific intermediate pore size molecular sieves include ITQ-13 (not yet assigned a structure type), MCM-22, ZSM-5, ZSM-11, ZSM-12, ZSM-22, ZSM-23, ZSM-34, ZSM-35, ZSM-38, ZSM-48, ZSM-50, and ZSM-57. Examples of large pore molecular sieves include molecular sieves having a pore size of at least about 7 Å such as AET, AFI, BEA, EMT, FAU, LTL, MAZ, MEI, MOR, OFF, and VFI structure type molecular sieves. Non-limiting examples of large pore molecular sieves include for example mazzite, offretite, Zeolite L, VPI-5, Zeolite Y, Zeolite X, omega, Beta, ZSM-3, ZSM-4, ZSM-18, ZSM-20, and SAPO-37. Non-limiting examples of the preferred molecular sieves, particularly for methylating a toluene containing feedstock into xylenes, include AEL, BEA, FAU, FER, LTL, MFI, MOR, MTT, MTW, MWW, and TON structure types. For a naphthalene feedstock, preferred molecular sieve configurations would include, but not be limited to, BEA, FAU, MOR, and MWW structure types. In one preferred embodiment, the molecular sieve of the invention has an MFI topology (such as ZSM-5) or an MTT topology (such as ZSM-23), or a combination thereof, most preferably an MFI topology.

Preferred molecular sieves include intermediate and large pore configurations, preferably having an average pore diameter in the range of about 3.5 Å to about 15 Å, more preferably in the range from about 5 Å to about 7 Å.

Aluminosilicate molecular sieves have been described in detail in numerous publications, including, for example, co-pending U.S. patent application Ser. No. 09/866,907 (ITQ-13) and U.S. Pat. No. U.S. Pat. No. 3,702,886 (ZSM-5), U.S. Pat. No. 4,076,842 (ZSM-23), U.S. Pat. No. 4,397,827 and U.S. Pat. No. 4,358,397 (ZSM-48), and U.S. Pat. No. 4,954,325 (MCM-22). Silicon, aluminum, and phosphorous based molecular sieves and metal containing silicon, aluminum, and phosphorous based molecular sieves are also known in the art. Other molecular sieves include those described in R. Szostak, *Handbook of Molecular Sieves*, Van Nostrand-Reinhold, New York, N.Y. (1992), which is herein fully incorporated by reference.

The synthesis of molecular sieves is described in many of the references known to those skilled in the art. Generally, molecular sieves are synthesized by the hydrothermal crystallization of one or more of a source of aluminum, a source of phosphorous, a source of silicon, a templating agent, and a metal containing compound. Typically, a combination of sources of silicon, aluminum, and/or phosphorous, optionally with one or more templating agents and/or one or more metal containing compounds are placed in a sealed pressure vessel, optionally lined with an inert plastic such as polytetrafluoroethylene, and heated under a crystallization pressure and temperature until a crystalline material is formed, which is then recovered by filtration, centrifugation, and/or decanting.

Aluminosilicate molecular sieves can be crystallized over a wide range of silicon (Si) to aluminum (Al) ratios. This $Si/Al_2$ ratio is one factor that dictates the level of acidity or acid activity a particular molecular sieve will exhibit. Normally, the higher the $Si/Al_2$ ratio, the less acidic an aluminosilicate molecular sieve will be and usually less prone to coking. The crystal size and the dimensions of the channel system are also important variables affecting coke formation. A high $Si/Al_2$ ratio is generally preferred for alkylation processes using aluminosilicates. In one embodiment, the molecular sieve, as synthesized, is an aluminosilicate molecular sieve having a $Si/Al_2$ ratio greater than 12, preferably between 40 and 1000, and most preferably between 100 and 500, all as measured prior to any treatment of the molecular sieve to reduce its diffusivity. Different constraints and preferences will apply to molecular sieves containing phosphorous; for example in SAPOs, lower silica content correlates to lower acidity.

Method for Making Molecular Sieve Catalyst Compositions

The crystals of molecular sieve can be formed into a wide variety of forms. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded or the crystals can be calcined to remove organic template and then extruded. All of these forms will be referred to herein as "crystals."

In the case of many catalysts, it is desirable that crystalline molecular sieves be incorporated with binder material resistant to the temperature and other conditions employed in organic conversion processes. Such binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite, or anauxite. Such clays can be used in the raw state as originally mined or initially subjected to calcination, acid treatment, or chemical modification. In one embodiment, the binder is different from the active metal oxide.

In addition to the foregoing materials, the molecular sieves may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia, and silica-magnesia-zirconia. The molecular sieve may also be composited with materials such as the zeolitic materials which are disclosed in U.S. Pat. No. 5,993,642, which is herein fully incorporated by reference. In one embodiment, the matrix material is different from the active metal oxide.

The relative proportions between the molecular sieve component and the binder and/or matrix material will vary widely with the molecular sieve content ranging from about 1 to about 99 percent by weight, more preferably in the range of about 10 to about 70 percent by weight of molecular sieve component, and still more preferably from about 20 to about 50 percent.

In one embodiment, the binder, the molecular sieve, and the matrix material are combined in the presence of a liquid to form a molecular sieve catalyst composition. The combination is then subjected to calcination.

Upon combining the molecular sieve and the matrix material, optionally with a binder, in a liquid to form a slurry, mixing, preferably rigorous mixing is needed to produce a substantially homogeneous mixture containing the molecular sieve composition. Non-limiting examples of suitable liquids include one or a combination of water, alcohol, ketones, aldehydes, and/or esters. The most preferred liquid is water.

The molecular sieve composition, the matrix material, and the optional binder are in the same or different liquid and are combined in any order, together, simultaneously, sequentially, or a combination thereof. In a preferred embodiment, the same liquid, preferably water, is used. The molecular sieve composition, matrix material, and optional binder are combined in a liquid as solids, substantially dry or in a dried form, or as slurries, together or separately. If solids are added together as dry or substantially dried solids, it is preferable to add a limited and/or controlled amount of liquid.

In one embodiment, the uniform slurry of the molecular sieve, binder, and matrix materials is fed to a forming unit that produces the formed molecular sieve catalyst composition. The forming unit may be a spray dryer maintained at a temperature sufficient to remove most of the liquid from the slurry and from the resulting molecular sieve catalyst composition. The resulting catalyst composition when formed in-this way takes the form of microspheres. In an alternative embodiment, the molecular sieve catalyst composition may be formed into tablets, pellets, granules, beads or the like through a process such as auger extrusion. To facilitate such an extrusion process, extrusion aids such as polymers, for example poly vinyl acetate (PVA), or cellulose derivatives may be added to the formulation during mixing.

Once the molecular sieve catalyst composition is formed in a substantially dry or dried state, to further harden and/or activate the formed molecular sieve catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

In a preferred embodiment, the molecular sieve catalyst or molecular sieve catalyst composition is heated in air from room temperature to about 540° C., at a heating rate of about 5° C./min and then the temperature is maintained at about 540° C. for about 4 hours to about 6 hours.

The molecular sieves and molecular sieve catalyst compositions prepared by the process of the present invention may be further ion exchanged before or after calcination either to replace at least in part the original alkali metal present in the zeolite with a different cation, e.g. a metal such as nickel, copper, zinc, palladium, platinum, calcium, or rare earth metal, or to provide a more acidic form of the molecular sieve by exchange of alkali metal with intermediate ammonium, followed by calcination of the ammonium form to provide the acidic hydrogen form. The acidic form of the molecular sieve may be readily prepared by ion exchange using a suitable acidic reagent such as ammonium nitrate. The molecular sieve may then be calcined at a temperature of about 400° C. to about 550° C. to remove ammonia and create the hydrogen form. Particularly preferred cations will depend on the use of the zeolite and include hydrogen, rare earth metals, and metals of Groups 2, 3, 4, 8, 9, 10, 11, 12, 13, and 14 of the Periodic Table of the Elements.

In another preferred embodiment, the molecular sieve catalyst or molecular sieve catalyst composition is first selectivated with a selectivating agent prior to use in the alkylation process. The term "selectivating agent" is used herein to indicate substances that will increase the shape-selectivity (e.g., para-selectivity) of the molecular sieve catalyst. Some non-limiting examples of selectivation include treating the molecular sieve with phosphorus and/or boron oxide, coke, or various silicon-containing compounds.

Selectivation may also be accomplished by exposing the catalyst in a reactor bed to a thermally decomposable organic compound, e.g., toluene, at a temperature in excess of the decomposition temperature of said compound, e.g., from about 480° C. to about 650° C., more preferably 540° C. to 650° C.; at a weight hourly space velocity (WHSV) in the range of from about 0.1 to 20 kg of feed per kg of catalyst per hour; at a pressure in the range of from about 1 to 100 atmospheres; and in the presence of 0 to about 2 moles of hydrogen per mole of organic compound, more preferably from about 0.1 to about 2 moles of hydrogen per mole of organic compound; and optionally in the presence of 0 to 10 moles of nitrogen or another inert gas per mole of organic compound. This process is conducted for a period of time until the desired quantity of coke has deposited on the catalyst surface.

Furthermore, selectivation may be accomplished using organosilicon compounds as selectivating agents. The organosilicon compounds used in one embodiment comprise polysiloxane, including silicone and siloxanes, and a silane including disilanes and alkoxysilanes. Organosilicon compounds include siloxanes as represented by the general formula:

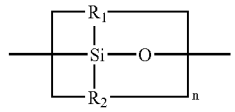

wherein $R_1$ is hydrogen or a halogen, hydroxyl, alkyl, halogenated alkyl, aryl aralkyl, halogenated aralkyl, alkaryl, or halogenated alkaryl group. The hydrocarbon substituents generally contain from 1 to about 10 carbon atoms, preferably methyl, ethyl, or phenyl groups. $R_2$ is selected from the same group as $R_1$, and n is an integer of at least 2 and generally in the range of 3 to about 1000. The molecular weight of the organosilicon compound employed is generally about 80 to about 20,000 and preferably about 150 to about 10,000. Examples of organosilicon compounds include, but are not limited to, dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylphenyl silicone, methylvinyl silicone, and ethylvinyl silicone. The silicone compound need not be linear but may be cyclic as for example hexamethyl cyclotrisiloxane, octamethyl cyclotetrasiloxane, hexaphenyl cyclotrisiloxane, and octaphenyl cyclotetrasiloxane. Mixtures of these compounds are also useful as are silicones with other functional groups.

Other organosilicon compounds, including silanes and alkoxy silanes, such as tetramethoxy silane, can also be utilized as selectivating agents. These useful silicon-containing selectivating agents include silanes characterized by the general formula:

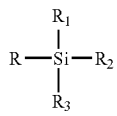

wherein R, $R_1$, $R_2$, and $R_3$ are independently selected from the group consisting of hydrogen, hydroxyl, halogen, alkyl, halogenated alkyl, alkoxy, aryl, and halogenated alkaryl groups. Mixtures of these compounds are also useful.

Preferred silicon-containing selectivating agents include dimethylphenylmethyl polysiloxane (e.g., Dow-550) and phenylmethyl polysiloxane (e.g., Dow-710), both available from Dow Chemical Co. in Midland, Mich.

Examples of suitable carriers for the selectivating agents, preferably silicon compounds, include linear, branched, and cyclic alkanes having five or more carbons. In the methods of the present invention it is preferred that the carrier be a linear, branched, or cyclic alkane having a boiling point greater than about 70° C. and most preferably containing 6 or more carbons. Optionally, mixtures of low volatility organic compounds, such as hydrocracker recycle oil, can be employed as carriers. The most preferred low volatility hydrocarbon carriers of selectivating agents are decane and dodecane.

The catalyst can be selectivated by single or multiple treatments with a liquid organosilicon compound in a liquid carrier followed by calcination of the treated material in an oxygen containing atmosphere. The catalyst can also be selectivated with both silica and coke. Other techniques such as steaming and impregnation with various compounds have also been found to alter the properties (e.g. activity, selectivity, and/or stability) of the molecular sieve structure.

Active Metal Oxides

Active metal oxides of the invention are those metal-oxides, different from typical binders and/or matrix materials, that, when used in combination with a molecular sieve, provide benefits in catalytic conversion processes. Preferred metal oxides are those metal oxides having a Group 2, Group 3, Group 4, Lanthanide Series, and/or Actinide Series metal from the Periodic Table of Elements using the IUPAC format described in the *CRC Handbook of Chemistry and Physics,* 79th Edition, CRC Press, Boca Raton, Fla. (1998). More preferred active metal oxides are Group 3 (preferably yttrium or lanthanum) oxides alone or Group 4 metal oxides such as zirconium and/or hafnium oxide in combination with a Group 2 and/or Group 3 metal oxide. In one embodiment, the most preferred active metal oxide is an active yttrium oxide. In another embodiment, the preferred active metal oxide is a zirconium and/or hafnium metal oxide mixed with lanthanum oxide. In yet another embodiment, the preferred active metal oxide is non-acidic or basic. Active metal oxides of this invention include other oxides such as MgO and hydrotalcite-derived mixed magnesium-aluminum non-acidic oxides.

While there are many different benefits in catalytic conversion processes, one of the most desirable is an extension of the catalyst composition life. Quantification of the extension in the molecular sieve catalyst composition life can be determined using the Half-life Enhancement Index (HLEI) as defined by the following equation:

HLEI=Half-life of Catalyst in Combination with Active Metal Oxide/Half-life of Catalyst where the half-life of the catalyst is the processing time until the conversion of feedstock by the catalyst falls below 50% of the initial conversion rate for that feedstock. Similarly the half-life of the catalyst in combination with active metal oxide, the multi-component molecular sieve catalyst composition, is the processing time under the same test conditions and using the same weight of molecular sieve until the conversion of feedstock falls below 50% of the initial conversion rate for that feedstock. HLEI is measured at conditions closely approximating the reaction conditions under which either the molecular sieve catalyst composition or the multi-component molecular sieve catalyst composition would commercially be used, provided that reaction conditions for both tests will be held constant, the weight hourly space velocity (WHSV) will be held constant based on the quantity of molecular sieve present in each test, and that quantity of molecular sieve will also be held constant. Initial conversion percentage will be the conversion percentage measured at some point within the first four hours of reaction runtime, preferably within the first hour, and measured at the same time on-stream for each of the molecular sieve catalyst composition and the multi-component molecular sieve catalyst composition being compared. All reaction conditions including WHSV with respect to the molecular sieve, not the multi-component molecular sieve catalyst composition, must be held constant for the individual half-life determinations to get a meaningful HLEI comparison between the molecular sieve or molecular sieve composition and the multi-component molecular sieve composition.

A metal oxide that is not active will have little or no effect on the lifetime of the catalyst composition, or will shorten the lifetime of the catalyst composition, and will therefore have an HLEI less than or approximately equal to 1. Active metal oxides of the invention are those metal oxides, different from typical binders and/or matrix materials, that, when used in combination with a molecular sieve, provide a multi-component molecular sieve catalyst composition that has an HLEI greater than 1. By definition, a molecular sieve catalyst composition that has not been combined with an active metal oxide will have an HLEI equal to 1.0.

In one embodiment, the active metal oxide, when combined with a molecular sieve, enhances the HLEI of the molecular sieve in an alkylation of toluene to produce xylenes, particularly para-xylene. In another embodiment, the multi-component molecular sieve catalyst composition of the invention, containing one or more active metal oxides has an HLEI greater than 1. In a preferred embodiment, the HLEI of the multi-component molecular sieve catalyst composition containing one or more active metal oxides is preferably greater than about 2, more preferably greater than about 10, even more preferably greater than about 20, and most preferably greater than about 100. In another preferred embodiment, the half-life of the multi-component molecular sieve composition under typical reactor conditions is preferably greater than 1 day, more preferably greater than 10 days, and most preferably greater than 2 months.

In one embodiment, the active metal oxide of the invention may not consist solely or substantially of oxides of silicon, aluminum, phosphorus, or combinations thereof.

In yet another embodiment, the active metal oxides of the invention are non-acidic or basic metal oxides as determined by the molar ratio of chemisorption of $CO_2$ and $NH_3$ over these metal oxide materials. $CO_2$, a mild acid, is used to titrate the basic sites present on the metal oxide being tested. Likewise, $NH_3$, a strong base, is titrated to indicate the acidic sites on the material. Many factors determine the actual amount of chemisorption such as surface area of the material (often significantly affected by the metal oxide preparation method), the temperature at which the chemisorption is tested, and the pressure at which the chemisorption is tested. For the purposes of this invention, a "non-acidic" oxide is defined as an oxide having a molar ratio of chemisorption of $CO_2$ per gram of metal oxide to the chemisorption of $NH_3$ per gram of metal oxide greater than about 0.5 when tested as described below.

Testing to determine the molar ratio of chemisorption of $CO_2$ per gram of metal oxide to the chemisorption of $NH_3$ per gram of metal oxide was conducted using a Mettler TGA/SDTA 851 thermogravimetric analysis system at ambient pressure. The metal oxide sample was calcined in flowing air to about 700° C. (except as noted in Table 1) for about three hours, at least until a constant sample weight was obtained. The temperature of the sample was then reduced in flowing air (helium could also be used) to the desired temperature of chemisorption. Next, the sample was allowed to equilibrate at the desired temperature in flowing helium and weighed. Chemisorption of carbon dioxide was measured at 100° C., and chemisorption of ammonia was measured at 250° C. After being weighed, the sample was subjected to a number of pulses (about 12 seconds/pulse) of a gaseous mixture containing helium and either carbon dioxide or ammonia until a constant weight was obtained. The gas mixtures contained about 10 weight percent carbon dioxide or ammonia with the remainder being helium. After each pulse of the gas mixture being tested, the metal oxide sample was flushed with flowing helium for about 3 minutes. About 20 separate pulses of the gas mixture was used in each test. The increase in weight of the sample in terms of mg/g metal oxide based on the metal oxide sample weight after calcination was used to determine the moles of $CO_2$ or $NH_3$ adsorbed per gram of metal oxide.

Molar ratios of chemisorption of $CO_2$ per gram of metal oxide to the chemisorption of $NH_3$ per gram of metal oxide for some examples of metal oxide materials tested are shown in Table 1. Preferred molar ratios of $CO_2/NH_3$ chemisorption, tested as described above, are greater than about 0.5, more preferred ratios are greater than about 0.75, and the most preferred ratios are greater than about 1.0.

TABLE 1

| Material Tested | Calcination Temperature, ° C. | $CO_2/NH_3$ Chemisorption Molar Ratio |
|---|---|---|
| $TiO_2$ | 700 | 0.33 |
| 2% $CeO_x/ZrO_2$ | 700 | 0.33 |
| 5% $CeO_x/ZrO_2$ | 700 | 0.41 |
| $La_2O_3$ | 700 | 0.86 |
| $La_2O_3$ | 600 | 1.21 |
| 10% $Y_xO_y/ZrO_2$ | 700 | 1.88 |
| $ZrO_2$ | 700 | 1.95 |
| $ZrO_2$ | 500 | 2.00 |
| 5% $Y_xO_y/ZrO_2$ | 700 | 3.13 |
| 5% $CaO_x/ZrO_2$ | 700 | 3.77 |
| 5% $La_xO_y/ZrO_2$ | 700 | 4.86 |
| MgO | 700 | 11.47 |
| $CeO_2$ | 700 | 12.27 |
| $Y_2O_3$ | 700 | 14.95 |

The active metal oxides are prepared using a variety of methods. It is preferable that the active metal oxide is made from an active metal oxide precursor, such as a metal salt. Other suitable sources of active metal oxides include compounds that form these metal oxides during calcination, such as oxychlorides and nitrates. A further suitable source of metal oxides includes salts containing the cation of the desired metal, such as halides, nitrates, and acetates. Alkoxides are also sources of metal oxides, for example zirconium n-propoxide.

In one embodiment, the active metal oxide is hydrothermally treated under conditions that include a temperature of at least 80° C., preferably at least 100° C. The hydrothermal treatment typically takes place in a sealed vessel at greater than atmospheric pressure, however, a preferred mode of treatment involves the use of an open vessel under reflux conditions. Agitation of the active metal oxide in the liquid medium, for example, by the action of refluxing liquid and/or stirring, promotes the effective interaction of the oxide with the liquid medium. The duration of the contact of the oxide with the liquid medium is preferably at least 1 hour, preferably at least 8 hours. The liquid medium for this treatment preferably has a pH of about 7 or greater, preferably 9 or greater. Non-limiting examples of suitable liquid media include water, hydroxide solutions (including hydroxides of $NH_4^+$, $Na^+$, $K^+$, $Mg^{2+}$, and $Ca^{2+}$), carbonate and bicarbonate solutions (including carbonates and bicarbonates of $NH_4^+$, $Na^+$, $K^+$, $Mg^{2+}$, and $Ca^{2+}$), pyridine and its derivatives, and alkyl/hydroxyl amines.

In yet another embodiment, the active metal oxide is prepared by first preparing a liquid solution comprising a source of an active metal oxide, such as a salt of the metal. Suitable sources include, but are not limited to, salts or mixtures of salts containing a Group 2, Group 3, Group 4, Lanthanide Series, or Actinide Series metal, such as nitrates, sulfates, and halides. This solution containing a source of an active metal oxide is then subjected to conditions sufficient to cause precipitation of the solid oxide material, such as by the addition of a precipitating reagent to the solution, preferably a base such as sodium hydroxide or ammonium hydroxide. Water is a preferred solvent for these solutions. The temperature at which the liquid medium is maintained during the precipitation is preferably less than about 200° C., more preferably in the range of from about 0° C. to about 200° C. This liquid medium is preferably maintained at an ambient temperature, for example room temperature, or the liquid is cooled or heated. A preferred range of temperatures for precipitation is from about 20° C. to about 100° C. The resulting gel is preferably then hydrothermally treated at temperatures of at least 80° C., preferably at least 100° C. The hydrothermal treatment typically takes place in a sealed vessel at greater than atmospheric pressure or at ambient pressures. The gel, in one embodiment, is hydrothermally treated for up to 10 days, preferably up to 5 days, most preferably up to 3 days. The resulting material is then recovered, for example by filtration or centrifugation, washed, and dried. The resulting particulate material is preferably then calcined, preferably in an oxidizing atmosphere, at a temperature of at least 400° C., preferably at least 500° C., more preferably from about 600° C. to about 900° C., and most preferably from about 650° C. to about 800° C. The calcination time is preferably up to 48 hours, more preferably for about 0.5 hours to about 24 hours, and most preferably for about 1 hour to about 10 hours. In a most preferred embodiment, calcination is carried out at about 700° C. for about 1 hour to about 3 hours.

Although preferred methods of preparing metal oxides are described above, other methods for preparing the active metal oxides are known in the art and may be used within the scope of this invention.

In an embodiment, it is preferred to utilize two or more active metal oxides, preferably one Group 4 metal oxide and one or more selected from Group 2, Group 3, Lanthanide Series, and Actinide Series metal oxides. When two or more metal oxides are used, they may either be co-precipitated or precipitated separately and combined with each other at any later stage of processing including as calcined solid particles. When two or more metal oxides are used, the metal oxides may be combined with each other before or after any one or more metal oxides have been combined with the molecular sieve, including any combination which also includes a binder and/or matrix material. Any method of combining the active metal oxides with each other, such as impregnation, regardless of whether or not other materials are also combined with the metal oxides before, after, or at the time of combining the metal oxides, is within the scope of this invention.

In another embodiment, the metal oxides are combined in slurry or hydrated state or in a substantially dry or dried state, preferably the metal oxides are combined in a hydrated state. In a preferred embodiment, the mixture of metal oxides can be considered as having atomic level mixing of the two or more metals within the oxide, in which such atomic level mixing is achieved during synthesis of the mixed metal oxide. Such a mixed metal oxide will be considered to be an active metal oxide if the mixed metal oxide, when used in combination with a molecular sieve, provides an HLEI greater than 1.0 in catalytic conversion processes, regardless of whether or not all of the metal oxides incorporated into the mixed metal oxide are individually active.

In an embodiment where two or more metal oxides are combined, they may be combined in any proportion. Mole percent of any one metal oxide as compared to the total moles of metal oxides used in preparing the active metal oxide may range from about 0% to about 100%, preferably from about 1% to about 99%, more preferably from about 3% to about 97%, and most preferably from about 5% to about 95%.

In an embodiment, where the active metal oxide contains one or more Group 4 metal oxides and a second metal oxide consisting of any combination of one or more metal oxides selected from Group 2, Group 3, Lanthanide Series, and Actinide Series metal oxides, the mole ratio of the Group 4 metal oxides to the second metal oxide, taken as a group, is in the range of from 1000:1 to 1:1000 based on the total moles of the Group 4 and second metal oxides, preferably the mole ratio is in the range of from about 500:1 to about 1:2, more preferably from about 100:1 to about 1:1, and most preferably from about 50:1 to about 2:1.

In yet another embodiment, the active metal oxide, preferably containing a Group 4 metal oxide and a second metal oxide consisting of any combination of one or more metal oxides selected from Group 2, Group 3, Lanthanide Series, or Actinide Series metal oxides, has 1 percent to 25 percent by weight of the second metal oxide combination based on the total weight of the active metal oxide, more preferably from about 1 percent to about 20 percent, and most preferably from about 1 percent to about 15 percent.

Some preferred combinations of metal oxides include a zirconium and/or hafnium metal oxide from Group 4 with either a Group 2 calcium oxide or a Group 3 lanthanum and/or yttrium oxide.

In a preferred embodiment the metal oxides are calcined either before or after being combined.

Multi-Component Molecular Sieve Composition

The multi-component molecular sieve composition of the invention includes any one of the molecular sieves and/or molecular sieve compositions previously described mixed with any one or more of the active metal oxides described above. In one embodiment, more than one type of molecular sieve is used in the multi-component molecular sieve catalyst composition. Preferably, the molecular sieves are those resulting from the synthesis mixture of phosphorous-, aluminum-, and/or silicon-containing components, preferably while stirring and/or agitating and/or seeding with a crystalline material, optionally with an alkali metal, in a solvent such as water, and optionally with one or more templating agents, to form a synthesis mixture that is then heated under crystallization conditions of pressure and temperature as are known in the art. More preferably, the molecular sieve is an intermediate pore size metallosilicate molecular sieve, and most preferably an intermediate pore size aluminosilicate molecular sieve. Even more preferably, the active metal oxide is a co-precipitated combination of zirconium and lanthanum oxides, and the molecular sieve composition is a ZSM-5 catalyst modified as described U.S. Pat. No. 6,423,879, hereafter referred to as "steamed ZSM-5."

In one embodiment, the crystals of molecular sieve are first formed and are then combined with the active metal oxide, preferably in a substantially dry, dried, or calcined state, most preferably the crystals of molecular sieve and solid particles of active metal oxide are physically mixed in their calcined state to form the multi-component molecular sieve catalyst composition of the invention. In another embodiment, one or more active metal oxides or their precursors are added to the synthesis mixture for making a molecular sieve as described above and co-precipitated with the molecular sieve. Alternatively the crystals of molecular sieve and active metal oxides are mixed before drying.

Without being bound by any particular theory, it is believed that intimate mixing of the molecular sieve, either as crystals or as a molecular sieve catalyst composition, and one or more active metal oxides improve conversion processes using the multi-component molecular sieve catalyst composition of the invention. Intimate mixing may be achieved by any method known in the art, such as mixing with a mixer muller, drum mixer, ribbon/paddle blender, kneader, or the like.

In one embodiment, the multi-component molecular sieve catalyst composition has a weight ratio of the active metal oxide to the molecular sieve in the range of from about 1:1000 to about 8:1, preferably in the range from about 1:100 to about 2:1, and more preferably from about 1:50 to about 1:1.

In one embodiment, where the molecular sieve synthesized above is formulated into a molecular sieve catalyst composition, the active metal oxide is then combined with the formulated molecular sieve catalyst composition. It is also an embodiment of the invention that a first formulated molecular sieve catalyst composition is combined with an active metal oxide, and the resulting multi-component molecular sieve catalyst composition is then itself mixed with a binder and/or matrix material which could then be formed into desired shape and sized particles by well-known techniques such as spray drying, pelletizing, extrusion, and the like.

Without being bound by any particular theory, the addition of active metal oxides appears to have the effect of intercepting coke precursors, thereby interrupting the coke formation process. This effect is expected to allow the use of catalysts that may not have previously been commercially viable for use in aromatics alkylation.

The beneficial effect of active metal oxides in extending the lifetime of various catalyst compositions is expected to extend to all microporous materials including, but not limited to, metal-containing microporous materials, as well as to non-microporous materials such as silica-alumina and amorphous acid catalysts.

Process For Using the Multi-Component Molecular Sieve Catalyst Compositions

The molecular sieve compositions and catalyst compositions described above are useful in a variety of processes including: cracking, of for example a naphtha feed to one or more-light olefins or higher molecular weight (MW) hydrocarbons to lower MW hydrocarbons; hydrocracking, of for example heavy petroleum and/or cyclic feedstock; isomerization, of for example aromatics such as xylene; polymerization, of for example one or more olefins to produce a polymer product; reforming; hydrogenation; dehydrogenation; dewaxing, of for example hydrocarbons to remove straight chain paraffins; absorption, of for example alkyl aromatic compounds for separating out isomers thereof; alkylation, of for example aromatic hydrocarbons such as benzene and alkyl benzene, optionally with propylene to produce cumene or with long chain olefins; transalkylation, of for example a combination of aromatic and polyalkylaromatic hydrocarbons; dealkylation; hydrodecylization; disproportionation, of for example toluene to make benzene and para-xylene; oligomerization, of for example straight and branched chain olefins; and dehydrocyclization.

The preferred process of the invention is a process directed to the alkylation of a feedstock comprising one or more aromatic hydrocarbons to one or more alkyl aromatics in the presence of an alkylating agent. The most preferred process of the invention is a process directed to the alkylation of a feedstock comprising toluene to one or more xylene isomers, preferably predominantly para-xylene.

The term "aromatic" in reference to the alkylatable compounds which are useful herein is to be understood in accordance with its art-recognized scope which includes alkyl substituted and unsubstituted mono- and polynuclear compounds. Compounds of an aromatic character which possess a hetero atom are also useful provided they do not act as catalyst poisons under the reaction conditions selected.

Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, nitro, sulfono, and/or other groups which do not interfere with the alkylation reaction.

Suitable aromatic hydrocarbons include, but are not limited to, benzene, toluene, xylene, naphthalene, anthracene, naphthacene, perylene, coronene, and phenanthrene.

Generally the alkyl groups which can be present as substituents on the aromatic compound contain from one to about 22 carbon atoms, preferably from one to about eight carbon atoms, and most preferably from one to about four carbon atoms.

Suitable alkyl substituted aromatic compounds include toluene, xylene, isopropylbenzene, normal propylbenzene, alpha-methylnaphthalene, ethylbenzene, cumene, mesitylene, durene, p-cyxene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene, p-butyltoluene, 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic bydrocarbons such as are produced by the alkylation of aromatic hydrocarbons with olefin oligomers. Such products are frequently referred to in the art as alkylate and include hexylbenzene, nonylbenzene, dodecylbenzene, pentadecyclbenzene, hexyltoluene, nonyltoluene, dodecyltoluene, pentadecytoluene, to name a few. Very often alkylate is obtained as a high boiling fraction in which the alkyl group attached to the aromatic nucleus varies in size from about $C_6$ to about $C_{12}$.

Reformate containing substantial quantities of benzene, toluene, xylene and/or other alkylatable aromatic compounds also constitutes a useful feed for the alkylation process of this invention.

The multi-component molecular sieve catalyst compositions described above are particularly useful in alkylation processes using oxygen- and/or sulfur-containing alkylating agents. Suitable alkylating agents include, but are not limited to, alcohols (such as methanol, ethanol, and isopropanol), alcohol precursors (such as syngas, preferably in combination with an alcohol synthesis catalyst), ethers (such as-dimethyl ether), esters, and carbonates (such as dimethyl carbonate). Typically, an alkylating agent stream might contain one or more aliphatic-containing compounds that include alcohols, amines, carbonyl compounds (for example aldehydes, ketones, and carboxylic acids), ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms. Non-limiting examples of aliphatic-containing compounds include alcohols such as methanol and ethanol; alkyl-mercaptans such as methyl mercaptan and ethyl mercaptan; alkyl-sulfides such as methyl sulfide; alkyl-amines such as methyl amine; alkyl-ethers such as dimethyl ether, diethyl ether and methylethyl ether; alkyl-halides such as methyl chloride and ethyl chloride; alkyl ketones such as dimethyl ketone; formaldehydes; and various acids such as acetic acid.

In a preferred embodiment of the process of the invention, the alkylating agent contains one or more oxygenates, more specifically one or more organic compounds containing at least one oxygen atom. In the most preferred embodiment of the process of invention, the oxygenate in the alkylating agent is one or more alcohols, preferably aliphatic alcohols where the aliphatic moiety of the alcohols has from 1 to 20 carbon atoms, preferably from 1 to 10 carbon atoms, and most preferably from 1 to 4 carbon atoms. The alcohols useful as alkylating agents in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In a preferred embodiment, the alkylating agent is selected from one or more of methanol, ethanol, dimethyl ether, diethyl ether, or a combination thereof; more preferably methanol and/or dimethyl ether; and most preferably methanol.

Non-limiting examples of alkylated aromatic hydrocarbons include toluene, xylenes, ethylbenzene, propylbenzenes, butylbenzenes, ethyltoluenes, diethylbenzenes, methylnapthlalenes, and dimethylnaphthalenes.

In one preferred embodiment, the molecular sieve is an aluminosilicate; the active metal oxide is an active Group 4 metal oxide that has been modified by a Group 2, Group 3, Lanthanide Series, and/or Actinide Series metal oxide; and the alkylating agent is methanol. In a more preferred embodiment, the molecular sieve is steamed ZSM-5 and the active metal oxide is yttrium oxide or a co-precipitated combination of lanthanum oxide with zirconium and/or hafnium oxide.

The feedstock, in one embodiment, contains one or more diluents, typically used to reduce the concentration of the feedstock, which are generally non-reactive to the feedstock or multi-component molecular sieve catalyst composition. Non-limiting examples of diluents include helium, argon, hydrogen, nitrogen, carbon monoxide, carbon dioxide, water, essentially non-reactive paraffins (especially alkanes such as methane, ethane, and propane), essentially non-reactive aromatic compounds, and mixtures thereof. The diluent is used either in a liquid or a vapor form, or a combination thereof and may be either added directly to a feedstock entering into a reactor or added directly into a reactor, either at the front end or in staged additions down the length of the bed. The preferred diluents are hydrogen and water, with hydrogen and water together being more preferred, and a homogenous gas phase mixture of water and hydrogen being most preferred. Hydrogen gas used as a diluent also acts as an anti-coking agent. Surprisingly, the addition of water as a diluent in the reactor farther enhances the HLEI benefits seen with the use of multi-component molecular sieve catalyst compositions. Preferably, hydrogen and/or added water are present in a molar ratio between about 1:100 and about 10:1 with respect to total moles of the aromatic compound(s) and the alkylating agent(s) combined (hereafter together referred to as "reactants") and more preferably, hydrogen and water combined are present in a molar ratio between about 1:1 and about 5:1 with respect to the total moles of the reactants.

An alternative embodiment would include hydrogen and carbon monoxide in the feedstock mixture and at least one component in the catalyst that is capable of forming an alkylating agent, such as methanol, from hydrogen and carbon monoxide. For the purposes of this invention, the term "alkylating agent" will be understood to include alkylating agents formed in such parallel reactions whether or not the alkylating agent itself is part of the feed to the reactor, and any hydrogen added for the purpose of forming the alkylating agent would not be counted in the preferred molar ratios of hydrogen to reactants as described above.

The process for alkylating aromatics, especially using an alkylating agent comprising one or more oxygenates, in the presence of a multi-component molecular sieve catalyst composition of the invention, is carried out in a reactor system operating at conversion conditions and containing at least one reactor, where the reactor is a fixed bed reactor or a fluidized bed reactor (including a turbulent bed reactor), preferably a fixed bed reactor. In a preferred embodiment, a feedstock containing the alkylatable aromatic and an oxygen- or sulfur-containing alkylation agent are introduced to a reactor system containing a multi-component molecular sieve catalyst composition and one or more alkylated aromatics are recovered from the effluent exiting the reactor system.

This invention is applicable to a broad range of aromatic alkylation processes, preferably those in which methanol reacts with an aromatic compound, or mixture of aromatics, to add methyl groups. The conversion of benzene to toluene, xylenes, and/or $C_{9+}$ aromatics and the conversion of toluene to xylenes and/or $C_+$ aromatics are examples of aromatic methylation. In one embodiment, the aromatic compound is a relatively pure compound, and in another embodiment, the aromatic compound is contained in a mixture of aromatics and non-aromatics, such as reformate. In the fuels area, methylation of reformate or other $C_6$-$C_7$ streams could lower benzene content as well as increase fuel yields and octane values. For fuels, high selectivity to the para-isomer is not crucial, but para-selectivity is desirable for chemicals applications.

It will be recognized by those skilled in the art that the longer half-life of the multi-component molecular sieve catalyst composition would generally either allow its use in existing reactors, perhaps operating under modified reaction conditions, or allow the use of less complex reactor designs for new equipment. Reactor design is beyond the scope of this invention, but it will be recognized by those skilled in the art that this multi-component molecular sieve catalyst composition will allow a greater range of choices in the design and/or retrofit of reactors to be used for aromatics alkylation processes, and this invention is not limited to any particular reactor configuration. For example, it is contemplated that plug flow, fixed bed, or fluidized bed processes are used in combination, particularly in different reaction zones within a single or multiple reactor system.

The reaction temperature employed in the alkylation process, specifically within the reactor system, is generally in the range of from about 200° C. to about 1000° C., preferably from about 250° C. to about 700° C., more preferably from about 300° C. to about 700° C., yet more preferably from about 350° C. to about 650° C., yet even more preferably from about 400° C. to about 600° C., and most preferably from about 500° C. to about 580° C.

The reaction pressure employed in the alkylation process, specifically within the reactor system, varies over a wide range including autogenous pressure. The conversion pressure is based on the partial pressure of the feedstock exclusive of any diluent therein. Typically the conversion pressure employed in the process is in the range of from about 30 kPa to about 7 MPa, preferably from about 100 kPa to about 3.5 MPa, and most preferably from about 150 kPa to about 900 kPa.

When the multi-component molecular sieve catalyst composition does become coked, it can be regenerated using any regeneration technique suitable for the materials included in the multi-component molecular sieve catalyst as will be known to those skilled in the art.

EXAMPLES

In order to provide a better understanding of the present invention including representative advantages thereof, the following examples are offered. Example 1 will describe the synthesis of the mixed metal oxide for the multi-component catalysts. Example 2 (Comparative) will demonstrate the performance of a ZSM-23 molecular sieve catalyst composition and Example 3 will demonstrate the performance of the multi-component molecular sieve catalyst composition containing the ZSM-23 molecular sieve catalyst composition. Examples 4 and 5, 6 and 7, and 9 and 10, respectively, will similarly provide comparisons between molecular sieve catalyst compositions without an active metal oxide and multi-component molecular sieve catalyst compositions using the same type of molecular sieve catalyst composition physically mixed by stirring with particles of an active metal oxide mixture.

Example 1

Preparation of Active Metal Oxide

Fifty grams of $ZrOCl_2 \cdot 8H_2O$ were dissolved with stirring in 300 ml of distilled water. Another solution containing 4.2 grams of $La(NO_3)_3 \cdot 6H_2O$ and 300 ml of distilled water was prepared. These two solutions were combined with stirring. The pH of the final mixture was adjusted to approximately 9 by the addition of concentrated ammonium hydroxide (28.9 grams). This slurry was then put in polypropylene bottles and placed in a steam box (100° C.) for 72 hours. The product formed was recovered by filtration, washed with excess water, and dried overnight at 85° C. A portion of this product was calcined to 700° C. in flowing air for 3 hours to produce a mixed metal oxide ($La_xO_y/ZrO_2$) containing a nominal 5 weight percent lanthanum based on the final weight of the mixed metal oxide.

For Examples 2 through 10, catalyst performance data were obtained using a downflow fixed-bed reactor with the following operating conditions, unless otherwise noted:
Temperature=500° C.
Pressure=100 kPa
$H_2$ to reactants molar ratio=0.8
Pure methanol and toluene feeds at 1:3 molar ratio
WHSV=3.9 $h^{-1}$ based on molecular sieve catalyst composition
Catalyst load=2.0 g of molecular sieve catalyst composition for all tests For the 1:3 molar feed mixture, the maximum toluene conversion expected from reaction with methanol would be about 33%. Methanol utilization is reported as (moles of methanol converted)/(moles of xylene formed—moles of benzene formed). Benzene is subtracted to account for any xylene formed by the disproportionation of toluene to xylene plus benzene.

For the multi-component molecular sieve catalyst compositions, a physical mixture of 2.0 g of the molecular sieve-catalyst composition and 0.4 g of the mixed metal oxide was used. The toluene and methanol weight hourly space velocities were kept constant relative to the amount of molecular sieve catalyst composition in the bed.

Example 2 (Comparative)

The reaction described above was run using a molecular sieve catalyst composition containing 65 weight percent ZSM-23 molecular sieve (further described in U.S. Pat. No. 4,076,842) with a $Si/Al_2$ ratio about 100 which had been bound with an alumina-rich binder constituting 35 weight percent of the composition. The catalyst load was 2.0 g. The resulting toluene conversion, para-xylene selectivity, and methanol utilization at 2, 20, 40, 60, and 80 hours are shown in Table 2.

Example 3

This example used the same reaction conditions as Example 2, but 0.4 g of the $La_xO_y/ZrO_2$ product from Example 1 was added to 2.0 g of the ZSM-23 molecular sieve catalyst composition (as described in Example 2) as a physical mixture of particles to form a multi-component molecular sieve catalyst composition. The catalytic performance of the multi-component molecular sieve catalyst composition (ZSM-23 with $La_xO_y/ZrO_2$) at 2, 20, 40, and 170 hours is also shown in Table 2.

The data show that addition of $La_xO_y/ZrO_2$ to the aluminosilicate catalyst bed improved the catalyst activity, selectivity to para-xylene (which increased steadily with time to about 68% at the end of the test), and the catalyst life. The multi-component molecular sieve catalyst composition containing $La_xO_y/ZrO_2$ maintained approximately constant toluene conversion activity for 170 hrs, while the molecular sieve catalyst composition activity in Example 2 dropped to approximately half the initial toluene conversion after 27 hours and approximately zero at 80 hours. The HLEI in this test was greater than 6.3, and has not been extrapolated to the time at which toluene conversion by the multi-component molecular sieve composition would have dropped to half of its initial value.

Example 4 (Comparative)

An alumina-bound ZSM-5 catalyst composition that had been treated with silicone three times, with calcination after each silicone treatment, and steamed for 24 hours at 1000° F. was tested at the same conditions as Example 2 to provide a comparison case for this molecular sieve catalyst composition.

Example 5

Two grams of the same catalyst composition as described in Example 4 was mixed with 0.4 grams of the $La_xO_y/ZrO_2$ of Example 1, and tested at the same conditions as Example 3. The results for Examples 4 and 5 at 2, 20, 60, and 106 hours are shown in Table 2. The toluene conversion for the molecular sieve catalyst composition in Example 4 (silicone-treated ZSM-5) dropped to approximately half of the initial conversion rate after about 63 hours, while the toluene conversion for the multi-component molecular sieve catalyst composition stayed roughly constant at about 15% for over 106 hours, indicating that the HLEI in this comparison is greater than 1.7. Methanol utilization and para-xylene selectivity were also higher for the multi-component molecular sieve catalyst composition.

Example 6 (Comparative)

A molecular sieve catalyst composition with 25 weight percent ZSM-5 molecular sieve crystals having a $Si/Al_2$ ratio of 450 was spray dried with 5 weight percent phosphorus and clay and then steamed at 1090° C. to produce steamed ZSM-5. This molecular sieve catalyst composition was run in a fixed bed downflow reactor at a temperature of 585° C., a pressure of 280 kPa, an $H_2$ to reactants molar ratio of 2:1, with pure methanol and toluene feeds at a 1:2 molar ratio, an $H_2O$ to reactants molar ratio of 2:1, and a WHSV of 8 $h^{-1}$. The catalyst load was 2.0 g. Catalyst performance data for 2, 10, 20, and 30 hours are shown in Table 2.

Example 7

The same temperature, pressure, and flow rates were maintained as in Example 6, but 0.4 g of the $La_xO_y/ZrO_2$ material of Example 1 was added to 2.0 g of the comparison molecular sieve catalyst composition described in Example 6 as a physical mixture of particles. The catalytic performance of the molecular sieve catalyst composition comparative sample and of the multi-component molecular sieve catalyst composition are shown in Table 2.

The data show that addition of $La_xO_y/ZrO_2$ to the aluminosilicate catalyst bed improved toluene conversion, methanol utilization, and catalyst life. The multi component molecular sieve catalyst composition containing $La_xO_y/ZrO_2$ maintained approximately constant toluene conversion for 170 hours, at which point the $H_2O$ co-feed was discontinued in an effort to cause the catalyst to require regeneration. Even so, the toluene conversion had not yet dropped to 50% of the initial conversion rate at 300 hours. In contrast, the performance of the molecular sieve catalyst composition alone (Example 6) dropped to very low toluene conversion over a period of 30 hours, reaching 50% of the initial toluene conversion at approximately 7.5 hours. Again, not extrapolating the half-life of the multi-component molecular sieve catalyst composition beyond the time tested, the HLEI is greater than 22.7. It should be noted that although the initial data points for these two examples were reported for different times, the HLEI would by inspection still have been 20 or more had those data points been taken at the same run time.

Example 8

The multi-component molecular sieve catalyst composition used in Example 7 was run for 380 hours, with the water pump shut down at 170 hours to speed de-activation, then regenerated in-situ at 530° C. with air flow of 100 cc/min for 10 hours. The regenerated multi-component molecular sieve catalyst composition's performance at the same reaction conditions as were used in Examples 6 and 7 shows that this multi-component molecular sieve catalyst composition is regenerable After 280 hours on-stream the toluene conversion was 20%, methanol utilization was 50%, and paraxylene selectivity was 91%.

Example 9 (Comparative)

An alumina-bound ZSM-48 catalyst which had been treated with silicone three times, with calcination after each silicone treatment, and steamed for 24 hrs at 1000° F., was run at the same conditions as Example 2 to provide a comparison case for this catalyst composition.

Example 10

Two grams of the catalyst described in Example 9 were mixed with 0.4 grams of the $La_xO_y/ZrO_2$ of Example 1 and run at the same conditions as Example 3. The results for Examples 9 and 10 are shown in Table 2. The toluene conversion for the silicone-treated ZSM-48 dropped below 50% of its initial rate at about 12 hours on stream, while for the mixed catalyst toluene conversion was approaching 50% of its initial rate when the test ended at 60 hours, resulting in a HLEI greater than 5.0.

TABLE 2

| Example # | Catalyst | Time on stream, hrs | Toluene Conversion wt % | P-selectivity wt % | Methanol utilization wt % | Time at which catalyst reaches half-life, hrs |
|---|---|---|---|---|---|---|
| 2 | ZSM-23 | 2 (Initial) | 16 | 27 | 33 | ≅27 |
|   |   | 20 | 14 | 48 | 32 |   |
|   |   | 40 | 4 | 46 | 12 |   |
|   |   | 60 | 2 | 45 | 5 |   |
|   |   | 80 | <1 | 43 | 3 |   |
| 3 | ZSM-23 + $La_xO_y/ZrO_2$ | 2 (Initial) | 17 | 25 | 47 | >>170 |
|   |   | 20 | 14 | 31 | 42 |   |
|   |   | 40 | 12 | 36 | 39 |   |
|   |   | 170 | 12 | 66 | 39 |   |
| 4 | Silicon treated ZSM-5 | 2 (Initial) | 18 | 65 | 52 | ≅63 |
|   |   | 20 | 18 | 66 | 55 |   |
|   |   | 60 | 10 | 62 | 28 |   |
|   |   | 106 | 3 | 58 | 10 |   |
| 5 | Silicon treated ZSM-5 + $La_xO_y/ZrO_2$ | 2 (Initial) | 17 | 68 | 52 | >>106 |
|   |   | 20 | 17 | 68 | 51 |   |
|   |   | 60 | 15 | 70 | 50 |   |
|   |   | 106 | 15 | 71 | 50 |   |
| 6 | Steamed ZSM-5 | 2 (Initial) | 20 | 95 | 40 | ≅7.5 |
|   |   | 10 | 8 | 92 | 16 |   |
|   |   | 20 | 5 | 92 | 10 |   |
|   |   | 30 | 3 | 92 | 6 |   |
| 7 | Steamed ZSM-5 + $La_xO_y/ZrO_2$ * $H_2O$ Co-feed shut off at 170 hrs | 1 (Initial) | 23 | n/a | 46 | >300 |
|   |   | 10 | 28 | n/a | 56 |   |
|   |   | 25 | 32 | 89 | 65 |   |
|   |   | 140 | 28 | 83 | 68 |   |
|   |   | 170 | 29 | n/a | n/a |   |
|   |   | 300* | 13* | 75* | 35* |   |
| 8 | Regenerated Steamed ZSM-5 + $La_xO_y/ZrO_2$ | 3 (Initial) | 22 | 85 | 42 | >>280 |
|   |   | 25 | 30 | 86 | 60 |   |
|   |   | 280 | 20 | 91 | 50 |   |
| 9 | ZSM-48 | 4 (Initial) | 19 | 37 | n/a | ≅12 |
|   |   | 8 | 13 | 37 | 40 |   |
|   |   | 20 | 6 | 42 | 10 |   |
|   |   | 48 | 1 | 43 | n/a |   |
| 10 | ZSM-48 + $La_xO_y/ZrO_2$ | 2 (Initial) | 19 | 35 | n/a | >60 |
|   |   | 10 | 17 | 40 | 52 |   |
|   |   | 20 | 15 | 42 | 46 |   |
|   |   | 50 | 12 | 46 | 40 |   |
|   |   | 60 | 11 | 46 | n/a |   |

The comparison molecular sieve catalyst compositions used in Examples 2, 4, 6, and 9 had half-lives of about 8 to about 60 hours, which can force an aromatic methylation process built around these compositions to have expensive moving or fluidized catalyst beds and separate regeneration vessels in order to accommodate frequent catalyst regeneration. However, the multi-component molecular sieve catalyst compositions demonstrated in Examples 3, 5, 7, 8, and 10 had significantly longer catalyst life. Increasing the HLEI by using multi-component molecular sieve catalyst compositions could allow companies to use simpler, cheaper fixed-bed reactors or swing fixed bed reactors, as opposed to a more expensive fluid bed plus regenerator for aromatic alkylation processes in general, and toluene methylation processes in particular.

It appears that para-xylene selectivity for the catalyst with metal oxides improved with time on stream, perhaps by a gradual coke-selectivation mechanism. Additional selectivation, for example by silicone selectivation, steaming, zeolite binding, further coking, or combinations of the preceding techniques, could further improve para-xylene selectivity.

We claim:

1. A process for alkylating an aromatic compound by contacting the aromatic compound with an alkylating agent under alkylation conditions in the presence of a multi-component molecular sieve catalyst composition comprising a molecular sieve physically mixed with one or more active metal oxides having a $CO_2/NH_3$ Chemisorption Molar Ratio of at least 0.5.

2. The process of claim 1 wherein the one or more active metal oxides comprises a non-acidic metal oxide.

3. The process of claim 1 wherein any of the one or more active metal oxides, tested individually or as a mixture, has a $CO_2/NH_3$, chemisorption molar ratio greater than about 0.75.

4. The process of claim 1 wherein any of the one or more active metal oxides, tested individually or as a mixture, has a $CO_2/NH_3$ chemisorption molar ratio greater than about 1.0.

5. The process of claim 1 wherein the one or more active metal oxides comprises one or more metal oxides selected from the group consisting of Group 2, Group 3, Group 4, Lanthanide Series, and Actinide Series metal oxides.

6. The process of claim 1 wherein the one or more active metal oxides comprises a Group 4 metal oxide and at least one additional metal oxide selected from the group consisting of Group 2, Group 3, Lanthanide Series, and Actinide Series metal oxides.

7. The process of claim 1 wherein the one or more active metal oxides comprises a zirconium or hafnium oxide in combination with a lanthanum oxide.

8. The process of claim 1 wherein the one or more active metal oxides comprises yttrium oxide.

9. The process of claim 1 wherein said one or more active metal oxides comprises at least one combination of one or more metal oxides where said combination was prepared by co-precipitation of said one or more metal oxides and said combination is itself active.

10. The process of claim 1 wherein said one or more active metal oxides comprises at least one active metal oxide which has been calcined.

11. The process of claim 1 wherein the weight ratio of active metal oxide to molecular sieve, excluding any binders or matrix material, is in the range of about 1:100 to about 2:1.

12. The process of claim 1 wherein the weight ratio of active metal oxide to molecular sieve, excluding any binders or matrix material, is in the range of about 1:50 to about 1:1.

13. The process of claim 1 wherein the multi-component molecular sieve catalyst composition has a Half-life Enhancement Index (HLEI) greater than about 2.

14. The process of claim 1 wherein the multi-component molecular sieve catalyst composition has an HLEI greater than about 10.

15. The process of claim 1 wherein the multi-component molecular sieve catalyst composition has an HLEI greater than about 20.

16. The process of claim 1 wherein the molecular sieve is a crystalline metallosilicate.

17. The process of claim 1 wherein the molecular sieve is an aluminosilicate.

18. The process of claim 1 wherein the molecular sieve comprises at least one intermediate pore molecular sieve.

19. The process of claim 1 wherein the molecular sieve comprises crystals with a framework type selected from the group consisting of MFI, MTT, and MWW.

20. The process of claim 1 wherein the molecular sieve comprises steamed ZSM-5.

21. The process of claim 1 wherein the molecular sieve comprises at least one molecular sieve selected from the group consisting of ITQ-13, MCM-22, ZSM-5, ZSM-23, and ZSM-48.

22. The process of claim 1 wherein the multi-component molecular sieve catalyst composition further comprises a binder or a matrix material or both, said binder and matrix material each being different from each active metal oxide contained in the multi-component molecular sieve catalyst composition.

23. The process of claim 1 wherein the alkylating agent comprises an oxygenate.

24. The process of claim 1 wherein a diluent is present during the step of contacting the aromatic compound with an alkylating agent.

25. The process of claim 1 wherein the alkylating agent comprises methanol or methanol precursors.

26. The process of claim 25 wherein a diluent comprising hydrogen, water, or both hydrogen and water is present during the step of contacting the aromatic compound with an alkylating agent.

27. The process of claim 26 wherein said diluent is present in a molar ratio of hydrogen and water combined between about 1:1 and about 5:1 with respect to total moles of reactants.

28. The process of claim 1 wherein the alkylation occurs in a fixed-bed reactor.

29. A process for alkylating aromatic hydrocarbons, said process comprising contacting said aromatic hydrocarbons with a multi-component molecular sieve catalyst composition comprising crystals of molecular sieve and particulates of one or more active metal oxides having a $CO_2/NH_3$ Chemisorption Molar Ratio of at least 0.5, said contacting occurring under conversion conditions and in the presence of an alkylating agent.

30. The process of claim 29 wherein the particulates of one or more active metal oxides comprise a non-acidic metal oxide.

31. The process of claim 29 wherein said particulates of one or more active metal oxides, tested as a mixture, have a $CO_2/NH_3$ chemisorption molar ratio greater than about 0.75.

32. The process of claim 29 wherein said particulates of one or more active metal oxides, tested as a mixture, have a $CO_2/NH_3$ chemisorption molar ratio greater than about 1.0.

33. The process of claim 29 wherein the particulars of one or more active metal oxides comprise one or more metal oxides selected from the group consisting of Group 2, Group 3, Group 4, Lanthanide Series, and Actinide Series metal oxides.

34. The process of claim 29 wherein the particulates of one or more active metal oxides comprise an active Group 4 metal oxide and at least one additional active metal oxide selected from the group consisting of Group 2, Group 3, Lanthanide Series, and Actinide Series metal oxides.

35. The process of claim 29 wherein the particulates of one or more active metal oxides comprise a zirconium or hafnium oxide in combination with a lanthanum oxide.

36. The process of claim 29 wherein the particulates of one or more active metal oxides comprise yttrium oxide.

37. The process of claim 29 wherein said particulates of one or more active metal oxides comprise at least one combination of one or more metal oxides where said combination was prepared by co-precipitation of said one or more metal oxides and said combination is itself active.

38. The process of claim 29 wherein said particulates of one or more active metal oxides comprise at least one active metal oxide which has been calcined.

39. The process of claim 29 wherein the weight ratio of the particulates of active metal oxide to the crystals of molecular sieve, excluding any binders or matrix material, is in the range of about 1:100 to about 2:1.

40. The process of claim 29 wherein the weight ratio of the particulates of active metal oxide to the crystals of molecular sieve, excluding any binders or matrix material, is in the range of about 1:50 to about 1:2.

41. The process of claim 29 wherein the crystals of molecular sieve comprise crystalline aluminosilicate.

42. The process of claim 29 wherein the crystals of molecular sieve comprise intermediate or large pore molecular sieves.

43. The process of claim 29 wherein the crystals of molecular sieve comprise crystals with a framework type selected from the group consisting of MFI, MTT, and MWW.

44. The process of claim 29 wherein the crystals of molecular sieve comprise crystals of at least one molecular sieve selected from the group consisting of ITQ-13, MCM-22, ZSM-5, ZSM-23, and ZSM-48.

45. The process of claim 29 wherein the multi-component molecular sieve catalyst composition further comprises a binder or a matrix material or both, combined in any order with the crystals of molecular sieve and the particulates of active metal oxide.

46. The process of claim 29 wherein the multi-component molecular sieve catalyst composition has a Half-life Enhancement Index (HLEI) greater than about 2.

47. The process of claim 29 wherein the multi-component molecular sieve catalyst composition has an HLEI greater than about 10.

48. The process of claim 29 wherein the multi-component molecular sieve catalyst composition has an HLEI greater than about 20.

49. The process of claim 29 wherein the aromatic hydrocarbons comprise at least one of toluene and naphthalene.

50. The process of claim 29 wherein the alkylating agent comprises an oxygenate.

51. The process of claim 29 wherein a diluent is present during the step of contacting the aromatic hydrocarbons with an alkylating agent.

52. The process of claim 29 wherein the alkylating agent comprises methanol or methanol precursors.

53. The process of claim 52 wherein a diluent comprising hydrogen, water, or both hydrogen and water is present during the step of contacting the aromatic hydrocarbons with an alkylating agent.

54. The process of claim 53 wherein said diluent is present in a molar ratio of hydrogen and water combined between about 1:1 and about 5:1 with respect to total moles of reactants.

55. A process for producing one or more alkylated aromatics, the process comprising the steps of:
(a) introducing to a reactor system a feedstock comprising at least one alkylatable aromatic and at least one oxygen- or sulfur-containing alkylation agent, said reactor system containing a multi-component molecular sieve catalyst composition comprising a molecular sieve catalyst and at least one active metal oxide oxides having a $CO_2/NH_3$ Chemisorption Molar Ratio of at least 0.5;
(b) withdrawing from the reactor system an effluent stream; and
(c) recovering one or more alkylated aromatics from the effluent stream.

56. The process of claim 55 wherein the at least one active metal oxide comprises one or more metal oxides selected from the group consisting of Group 2, Group 3, Group 4, Lanthanide Series, and Actinide Series metal oxides.

57. The process of claim 55 wherein the at least one active metal oxide comprises at least one of an active zirconium metal oxide or an active hafnium metal oxide.

58. The process of claim 55 wherein said at least one active metal oxide comprises at least one of an active yttrium metal oxide, an active lanthanum metal oxide, or an active scandium metal oxide.

59. The process of claim 55 wherein the molecular sieve catalyst comprises an aluminosilicate molecular sieve or a silicoaluminophosphate molecular sieve or both.

60. The process of claim 55 wherein said at least one alkylatable aromatic comprises at least one of toluene or naphthalene.

61. The process of claim 55 wherein the alkylating agent comprises at least one of methanol or dimethylether.

62. The process of claim 55 wherein a diluent comprising hydrogen, water, or both hydrogen and water is present during die step of contacting the aromatic compound with an alkylating agent.

63. A process for producing para-xylene, the process comprising the steps of combining in a reactor at least one of an oxygen-containing alkylation agent or a sulfur-containing alkylation agent with a feedstock containing at least some toluene or benzene or both, said reactor containing a multi-component molecular sieve catalyst composition comprising a molecular sieve and one or more active metal oxides having a $CO_2/NH_3$ Chemisorption Molar Ratio of at least 0.5.

64. The process of claim 63 wherein the multi-component molecular sieve catalyst composition further comprises a binder or a matrix material or both, combined in any order with any or all of the other components of the multi-component molecular sieve catalyst composition.

65. The process of claim 63 wherein die multi-component molecular sieve catalyst composition has an HLEI greater tan 20.

66. The process of claim 63 wherein a diluent comprising hydrogen, water, or both hydrogen and water is present during the step of contacting die aromatic compound with an alkylating agent.

67. The process of claim 66 wherein said diluent is present in a molar ratio of hydrogen and water combined between about 1:1 and about 5:1 with respect to total moles of reactants.

68. The process of claim 63 wherein the para-xylene selectivity of the multi-component molecular sieve catalyst composition exceeds about 60% for a period exceeding 150 hours at commercial operating conditions.

69. A process for alkylating an aromatic compound in the presence of the molecular sieve catalyst composition prepared by a method for making a multi-component molecular sieve catalyst composition, the method comprising the step of combining a) at least one active metal oxide oxides having a $CO_2/NH_3$ Chemisorption Molar Ratio of at least 0.5, b) a molecular sieve synthesized from the combination of at least two of the group consisting of a silicon source, a phosphorous source, and an aluminum source, optionally in the presence of a templating agent, and c) a binder or a matrix material or both.

70. A process for alkylating an aromatic compound in the presence of the molecular sieve catalyst composition prepared by a method of making a multi-component molecular sieve catalyst composition, the method comprising the steps of:

(a) synthesizing a molecular sieve by the method comprising the steps of:
  (i) forming a first reaction mixture of at least two of the group consisting of a silicon source, a phosphorous source, and an aluminum source; and
  (ii) removing the molecular sieve from the first reaction mixture;
(b) forming an active metal oxide having a $CO_2/NH_3$ Chemisorption Molar Ratio of at least 0.5 by the method comprising the steps of:
  (i) forming a second reaction mixture of at least one metal oxide precursor and a precipitating agent;
  (ii) removing the active metal oxide from the second reaction mixture; and combining the molecular sieve and the active metal oxide oxides.

* * * * *